(12) United States Patent
Kleshinski

(10) Patent No.: US 6,245,012 B1
(45) Date of Patent: Jun. 12, 2001

(54) FREE STANDING FILTER

(75) Inventor: Stephen J. Kleshinski, Scituate, MA (US)

(73) Assignee: NMT Medical, Inc., Boston, MA (US)

( * ) Notice: Subject to any disclaimer, the term of this patent is extended or adjusted under 35 U.S.C. 154(b) by 0 days.

(21) Appl. No.: 09/401,606

(22) Filed: Sep. 22, 1999

Related U.S. Application Data

(60) Provisional application No. 60/125,134, filed on Mar. 19, 1999.

(51) Int. Cl.[7] ................................................. A61M 29/00
(52) U.S. Cl. ............................................................ 600/200
(58) Field of Search ................................. 606/200, 112, 606/114, 127; 623/1; 604/104; 600/127, 114

(56) References Cited

U.S. PATENT DOCUMENTS

| | | | | |
|---|---|---|---|---|
| 4,425,908 | * | 1/1984 | Simon | 128/303 |
| 4,643,184 | * | 2/1987 | Mobin-Uddin | 128/303 |
| 4,727,873 | * | 3/1988 | Mobin-Uddin | 128/303 |
| 5,192,286 | * | 3/1993 | Phan et al. | 606/127 |
| 5,324,304 | * | 6/1994 | Rasmussen | 606/200 |
| 5,695,519 | | 12/1997 | Summers et al. | 606/200 |
| 5,800,525 | * | 9/1998 | Bachinski et al. | 606/200 |
| 5,814,064 | * | 9/1998 | Daniel et al. | 606/200 |
| 5,827,324 | | 10/1998 | Cassell et al. | 606/200 |
| 5,833,644 | | 11/1998 | Zadno-Azizi et al. | 604/52 |
| 5,846,260 | | 12/1999 | Maahs | 606/200 |
| 5,876,367 | | 3/1999 | Kaganov et al. | 604/8 |
| 5,911,734 | * | 6/1999 | Tsugita et al. | 606/200 |
| 5,928,261 | | 7/1999 | Ruiz | 606/200 |
| 6,013,093 | | 1/2000 | Nott et al. | 606/200 |
| 6,129,739 | * | 10/2000 | Khosravi | 606/200 |

FOREIGN PATENT DOCUMENTS

| | | |
|---|---|---|
| WO 98/38920 | 9/1998 | (WO) . |
| WO 98/39046 | 9/1998 | (WO) . |
| WO 98/39063 | 9/1998 | (WO) . |

* cited by examiner

*Primary Examiner*—Cary E. O'Connor
(74) *Attorney, Agent, or Firm*—Nixon Peabody, LLP; Daniel W. Sixbey

(57) ABSTRACT

A free standing filter is provided with a filter body having an elongate guidewire receiving member extending centrally therethrough to define an open ended channel configured to receive a plurality of different sized guidewires. An expandable and contractible frame surrounds the elongate guidewire receiving member and is connected at a proximal end to the elongate guidewire receiving member. A porous embolic capturing unit has an open end connected to the frame and a closed end connected to the elongate guidewire receiving member which extends through the porous embolic capturing unit.

15 Claims, 3 Drawing Sheets

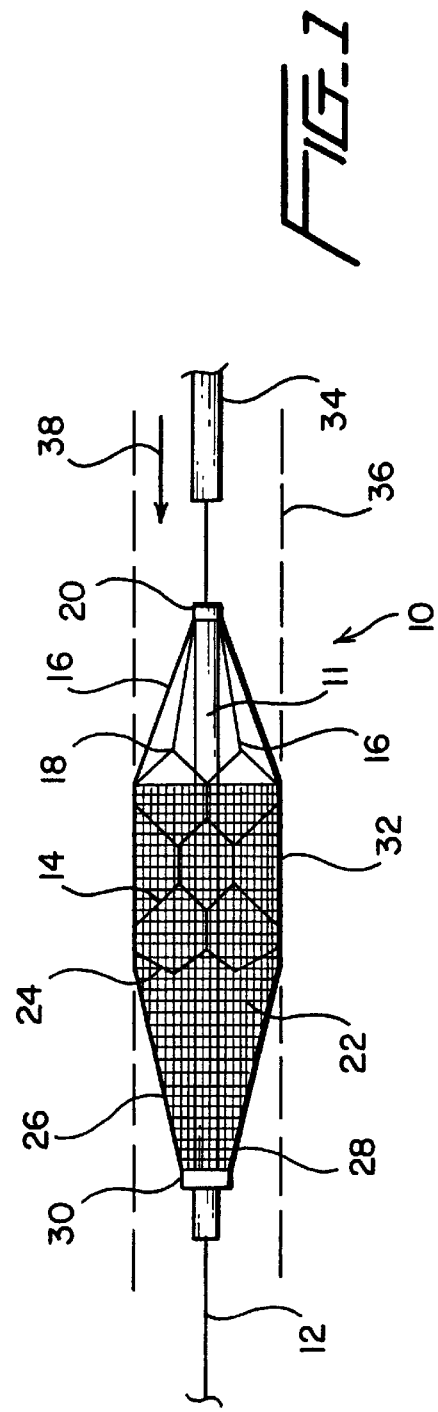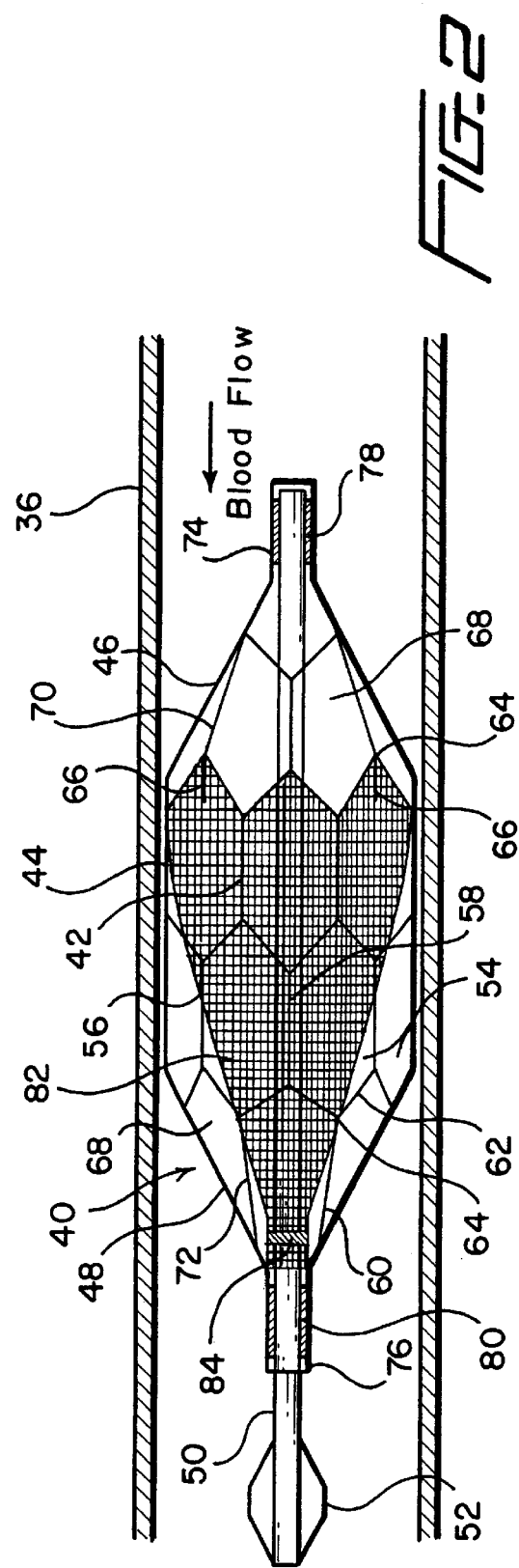

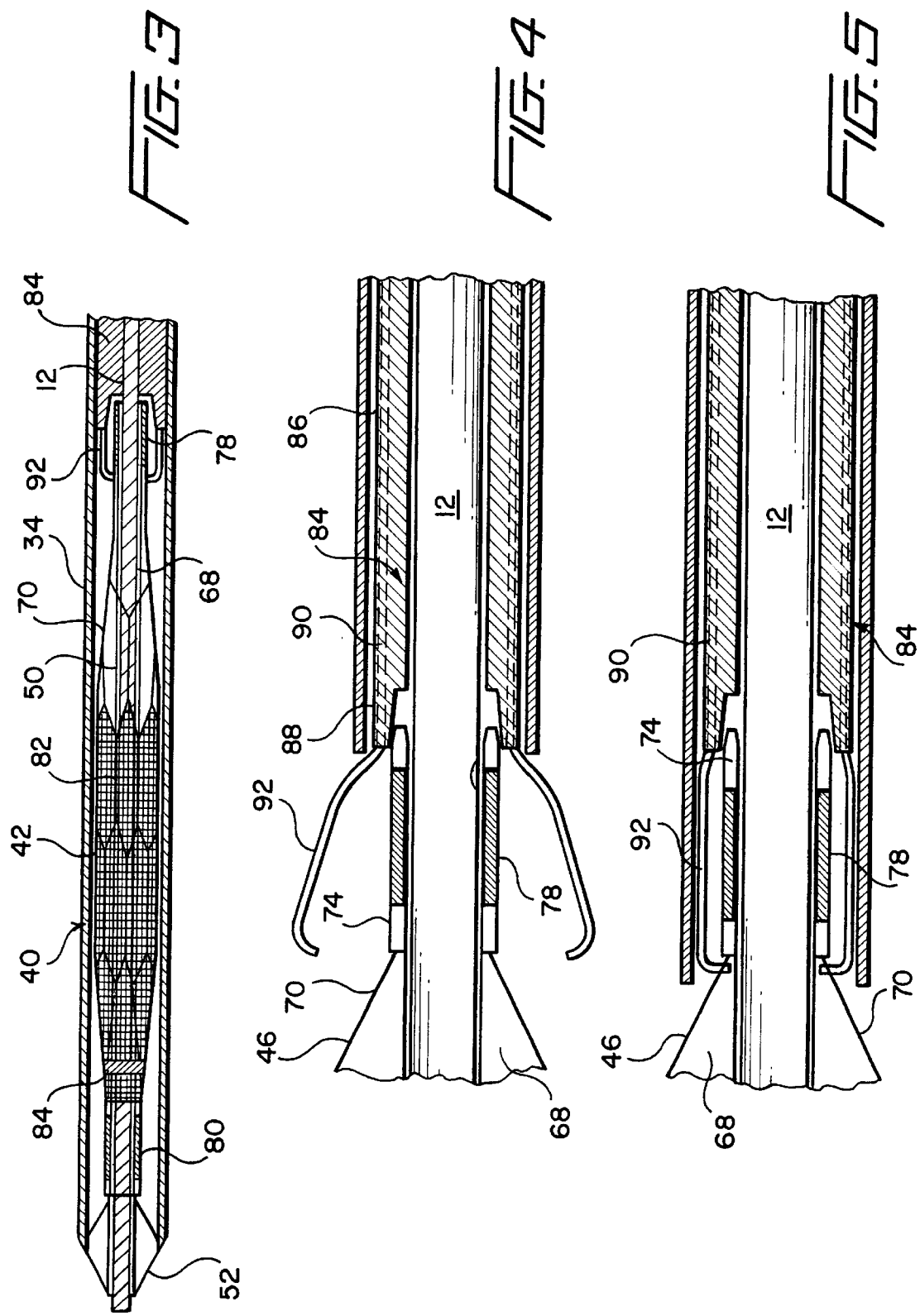

1

FREE STANDING FILTER

This application is a continuation in part application of U.S. Ser. No. 60/125,134 filed Mar. 19, 1999.

TECHNICAL FIELD

The present invention relates generally to small filters for insertion into a vein or artery, and more particularly to a filter which, when expanded, is free standing in engagement with a body vessel without penetrating the vessel wall.

BACKGROUND OF THE INVENTION

In recent years, a number of medical devices have been designed which are adapted for compression into a small size to facilitate introduction into a body vessel such as an arterial or vascular passageway and which are subsequently expandable into contact with walls of the passageway. These devices, among others, include stents, such as those shown by U.S. Pat. No. 5,540,712 and blood clot filters such as those shown by U.S. Pat. No. 5,669,933 which expand and are held in position by engagement with the inner wall of a vessel. It has been found to be advantageous to form such devices of a thermal shape memory material having a first, relatively pliable low temperature condition and a second, relatively rigid high-temperature condition. By forming such devices of temperature responsive material, the device in a flexible and reduced stress state may be compressed to fit within the bore of a delivery catheter when exposed to a temperature below a predetermined transition temperature, but at temperatures at or above the transition temperature, the device expands and becomes relatively rigid.

Known self expanding medical devices have been formed of Nitinol, an alloy of titanium and nickel which provides the device with a thermal memory. The unique characteristic of this alloy is its thermally triggered shape memory, which allows a device constructed of the alloy to be cooled below a temperature transformation level to a martensitic state and thereby softened for loading into a catheter in a relatively compressed and elongated state, and to regain the memorized shape in an austenitic state when warmed to a selected temperature, above the temperature transformation level, such as human body temperature. The two interchangeable shapes are possible because of the two distinct microcrystalline structures that are interchangeable with a small variation in temperature. The temperature at which the device assumes its first configuration may be varied within wide limits by changing the composition of the alloy. Thus, while for human use the alloy may be focused on a transition temperature range close to 98.6° F., the alloy readily may be modified for use in animals with different body temperatures.

In recent years advances have been made in the treatment of blood vessel stenosis or occlusion by plaque, thrombi, embolic, or other deposits which adversely reduce or block the flow of blood through a vessel. Balloon angioplasty or similar transluminal treatments have become common for some blood vessel lesions, but for all such procedures, plaque and emboli dislodged during the procedure are free to flow within the lumen of the vessel and possibly cause substantial injury to a patient.

In an attempt to contain and remove emboli and other debris, balloon angioplasty coupled with irrigation and aspiration has been performed as illustrated by U.S. Pat. No. 5,883,644 and International Publication No. WO 98/39046 to Zadno-Azizi et al. This procedure requires complete vessel occlusion cutting off all blood flow which imposes severe time constraints on the procedure. Additionally, the balloons involved in the procedure are affixed to elongate guidewires or small elongate catheters which extend for a substantial distance through blood vessels to the location of the stenosis or occlusion, and it is practically impossible to prevent some back and forth longitudinal motion of these elongate elements within a vessel during a procedure. This movement of the guidewire or catheter to which a balloon is attached causes the balloon to move back and forth and abrade emboli from the vessel wall downstream of the balloon containment area.

Angioplasty is often not a preferred treatment for lesions in the carotid artery because dislodged plaque can enter arterial vessels of the brain causing brain damage or even death. As indicated by U.S. Pat. No. 5,879,367 to Kaganov et al., carotid endarterectomy is a surgical procedure used to remove a lesion in the carotid artery, but this procedure also involves substantial risk of dislodged embolic material.

In an attempt to contain dislodged emboli during a procedure to clear blood vessel stenosis or occlusion, a variety of distal filters have been devised such as those shown by U.S. Pat. No. 5,814,064 and International Publication Nos. WO 98/38920 and WO 98/39053 to Daniel et al. as well as U.S. Pat. No. 5,827,324 to Cassell et al., U.S. Pat. No. 5,846,260 to Maahs and U.S. Pat. No. 5,876,367 to Kaganov et al. These filters are secured to the distal portion of a guidewire or catheter and are deployed distally from the stenosis or occlusion to capture embolic material. Once the distal filter is positioned and expanded into contact with the wall of the blood vessel, an angioplasty balloon, a stent, or other devices are introduced over the proximal end of the guidewire or catheter to which the filter is attached and moved into position in the area of the occlusion or stenosis spaced proximally from the filter.

Known guidewire or catheter attached distal filters have been subject to a number of disadvantages. First, since the elongate catheter or guidewire to which the filter is attached is used to guide over the wire devices during a subsequent procedure, it is extremely difficult if not impossible to prevent longitudinal movement of the wire or catheter after the filter has been deployed. This causes the filter to move back and forth within the vessel with resultant abrasion by the filter of the vessel wall, and such abrasion not only causes trauma to the vessel wall but also operates to dislodge debris which is free to flow distally of the filter. Thus filter movement after the filter is deployed somewhat defeats the purpose of the filter. Also, it is often desirable during a procedure to exchange guidewires, and such an exchange is not possible with an attached filter.

Finally the retrieval of known distal filters while retaining captured embolic material has proven to be problematic. Many cone shaped filters with wide, upstream proximal open ends tend to eject captured embolic material through the open end as the filter is collapsed. Also, many distal filters are formed by a mesh material which is expanded by a filter frame, and when the frame closes to collapse the filter for withdrawal through a catheter, the mesh folds creating outwardly projecting pleats. These pleats snag on the withdrawal catheter making retrieval of the filter difficult and often causing the filter to spill captured embolic material.

SUMMARY OF THE INVENTION

It is a primary object of the present invention to provide a novel and improved free standing filter for expansion within a blood vessel to capture dislodged embolic material.

Another object of the present invention is to provide a novel and improved free standing filter for use during a procedure to treat blood vessel stenosis or occlusion which does not cause trauma to the luminal wall during guidewire balloon and stent exchanges.

A further object of the present invention is to provide a novel and improved free standing filter for use during a procedure to treat blood vessel stenosis or occlusion which is formed to facilitate intra-procedural guidewire exchanges.

Yet another object of the present invention is to provide a novel and improved free standing filter for use during a procedure to treat blood vessel stenosis or occlusion which is formed to remain stationary after expansion independent of guidewire or catheter motion.

A further object of the present invention is to provide a novel and improved free standing filter for use during a procedure to treat blood vessel stenosis or occlusion which includes an elastomeric or knitted fiber mesh which collapses without pleating during the filter recovery process.

A still further object of the present invention is to provide a novel and improved free standing filter for use during a procedure to treat blood vessel stenosis or occlusion which is formed to capture and safely remove embolic material. The filter is provided with a proximal end designed for docking with a recovery system and which operates to positively close the open end of a filter mesh as the filter is collapsed during recovery.

These and other objects of the present invention are accomplished by providing a free standing filter with a filter body having an elongate guidewire receiving member extending centrally therethrough to define an open ended channel configured to receive a plurality of different sized guidewires. An expandable and contractible frame surrounds the elongate guidewire receiving member and is connected at a proximal end to the elongate guidewire receiving member. A porous embolic capturing unit has an open end connected to the frame and a closed end connected to the elongate guidewire receiving member which extends through the porous embolic capturing unit.

BRIEF DESCRIPTION OF THE DRAWINGS

FIG. 1 is a view in side elevation of the free standing filter of the present invention in the expanded configuration;

FIG. 2 is a partially sectional view in side elevation of a second embodiment of the free standing filter of the present invention;

FIG. 3 is a partially sectional view of the free standing filter of FIG. 2 within a delivery tube;

FIG. 4 is a sectional view of a positioning and recovery unit for the free standing filter of FIG. 2;

FIG. 5 is a sectional view of the positioning and recovery unit of FIG. 4 engaged with the free standing filter.

DESCRIPTION OF THE PREFERRED EMBODIMENTS

Figure 6:
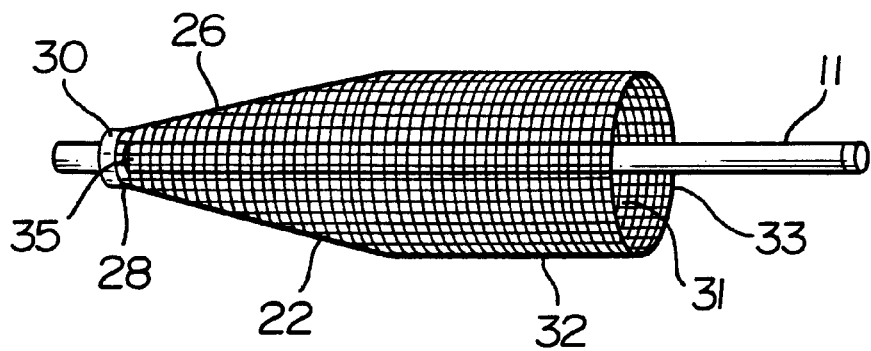
FIG. 6 is a perspective view of the fine mesh filter of FIG. 1.

Referring to FIG. 1, the free standing filter 10 of the present invention is formed around a central tube 11 which forms the longitudinal axis for the filter 10 and slidingly receives a guidewire 12. The frame of the filter is formed by a stent 14 which may be collapsed inwardly toward the tube 11 and which expands outwardly away from the tube to the substantially cylindrical open ended configuration shown in the drawings. Ideally, this stent is formed of thermal shape memory material and is of the type shown by U.S. Pat. No. 5,540,712, although other expandable stents can be used. The stent 14 is coupled at one end to the central tube 11 by elongate lead wires 16 which extend between an open proximal end 18 of the stent and a spaced coupling 20 which is secured to the central tube 11.

Extending around the stent 14 and attached thereto is a flexible, fine mesh filter material 22 which opens at the proximal end 18 of the stent and covers the body of the stent. Ideally, the stent extends over this mesh filter material. At the distal end 24 of the stent, the fine mesh filter material projects outwardly to form a flexible conical section 26 with an apex 28 connected to a coupling 30 which slides on the tube 11 in spaced relation to the stent distal end 24. Thus when the stent expands as shown in the drawings, the mesh filter material forms a substantially cylindrical section 32 which opens at the proximal end of the stent and a flexible, closed conical section 26 which extends beyond the distal end of the stent to catch and collect small particles. The mesh filter material therefore defines an enclosed chamber with a single open end 33 and a closed end 35. The fine filter mesh may be formed of suitable biocompatible material such as polyester or a PTFE material and is coated with thromboresistant materials such as, for example, Phosphoral Choline or Hyaluronic Acid. The mesh is a braided material or elastomeric mesh which normally conforms to the exterior shape of the central tube 11, but which stretches to expand outwardly away from the tube when the stent 24 expands. Thus the mesh is biased toward the tube 11, and when the stent collapses inwardly toward the tube, the mesh contracts back to the exterior shape of the tube and does not form pleats.

In the operation of the filter 10, the stent with the mesh filter material is inserted in a collapsed condition into a delivery tube 34 and guidewire 12 extends through the central tube 11. Then the delivery tube is used to deliver the filter 10 over the guidewire 12 to a desired position within a body vessel whereupon the filter is ejected from the delivery tube. Now the previously collapsed stent 14 expands into contact with the walls 36 of the vessel (shown in broken lines) thereby expanding the flexible mesh filter material which was previously collapsed within the delivery tube with the stent. The guidewire 12 may now be used to guide other devices into the vessel, and since the guidewire can move freely in a longitudinal direction within the tube 11, longitudinal movement of the guidewire will not result in movement of the expanded filter.

Once the stent 14 has expanded against the wall 36 of the vessel, the guidewire 12 can be removed and replaced with a new guidewire of a different size. The tube 11 is preferably formed of sufficient size to accept 0.014 inch diameter to 0.035 inch diameter guidewires. It may often be desirable to initially use a very fine guidewire (0.014") to cross a lesion and position the filter 10 and to then exchange this fine guidewire for a thicker wire.

The fine mesh filter material 22, when expanded, should have a pore size within a range of 50 $\mu$m to 300 $\mu$m to capture and retain embolic material sized in excess of the pore size while permitting blood flow in the direction of the arrow 38 line in FIG. 1 between the wires 16 and into the proximal end 18 of the stent 14. The blood and embolic material flows through the and into the flexible conical section 26 of the fine mesh filter material where the embolic material is trapped while the blood passes through the filter material.

To remove the filter 10 with the captured embolic material, the stent 14 is collapsed against the tube 11 for withdrawal through a catheter or delivery tube 34. Preferably the stent is formed of the thermal shape memory material such as nitinol or other materials, for example, including but not limited to Titanium, stainless steel, MP35N alloys or other similar materials and may be collapsed by cooling the stent to a temperature below a transition temperature. It is important to note that the embolic material has been captured within the conical section 28, so that when the stent collapses against the tube 11, it positively closes the mouth of the conical section preventing material from escaping as the filter is drawn into the tube 34. The stent forces the entire longitudinal extent of the section 32 against the tube 11 to prevent the escape of material from the conical section 28.

Figure 7:
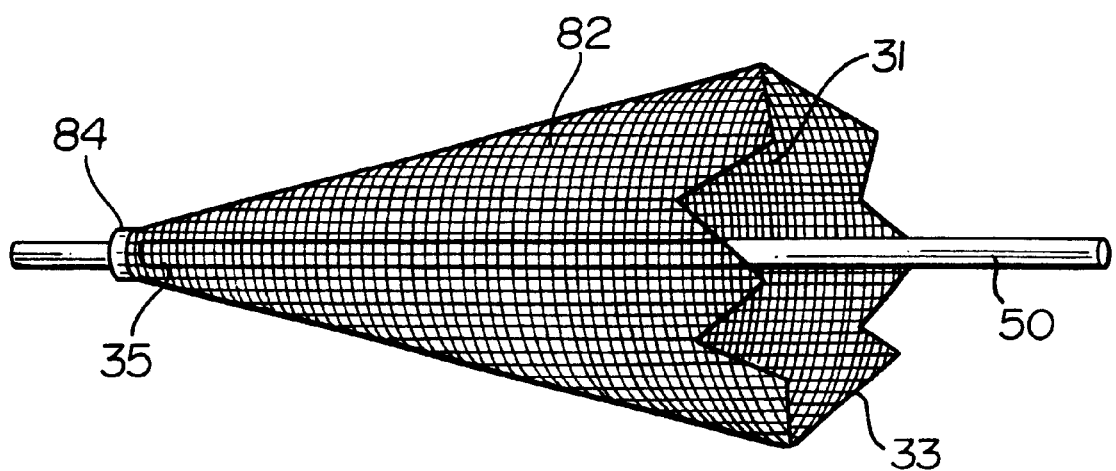
FIG. 7 is a perspective view of the fine mesh filter of FIG. 2.

Referring now to FIGS. 2, 3 and 7, a second embodiment of the free standing filter of the present invention is indicated generally at 40. For unimpeded passage through a catheter or delivery tube 34, it is beneficial to form a filter with a frame which completely surrounds and protects the filter mesh material. Thus the filter 40 includes a cellular frame 42 which is preferably formed of thermal shape memory material such as nitinol, and this frame when expanded includes a central section 44 having a substantially tubular configuration, a proximal end section 46 and a distal end section 48, both having a substantially conical configuration. A central tube 50, similar in size to the tube 11, forms the central longitudinal axis for the filter 40 and extends through the filter and outwardly from the proximal and distal sections of the frame 42. The distal end of the tube 50 is provided with a tapered atraumatic molded tip 52 configured to center and guide the filter within the delivery tube 34.

The central section 44 of the frame 42 includes a plurality of interconnected cells 54 which are substantially equal in size and which are defined by spaced sidewalls 56 and 58 which extend substantially parallel to the tube 50 and the longitudinal axis of the filter. Adjacent cells 54 in a row of cells extending around the central tube 50 are connected together by their adjacent sidewalls 56 and 58, and these sidewalls remain substantially parallel to the tube 50 in both the expanded and collapsed configuration of the filter 40 as illustrated in FIGS. 2 and 3. The opposite ends of each cell are formed by outwardly inclined endwall sections 60 and 62 which meet at an apex 64. Extending in a distal direction from the apex 64 of alternate cells 54 at the proximal end of the central section 44 are short, straight stabilizers 66 which engage the vessel wall 36 when the filter is expanded and aid to preclude movement of the filter in a distal direction.

The proximal end section 46 and distal end section 48 of the frame 42 are formed of cells 68 with tapered sidewalls 70 and 72 which extend at an angle to the central tube 50 to form the tapered conical end sections of the frame. Proximal end section 46 of the frame is secured to the tube 50 by a coupling 74, and distal end section 48 is secured to a coupling 76 which slides on the tube 50. The couplings 74 and 76 are provided with radiopaque markers 78 and 80 respectively.

Fine mesh filter material 82 of the type previously described for the filter 10 is positioned within the central and distal sections of the frame 42. This filter material is bonded to at least the first row of cells 54 in the proximal end of the central section 44 of the frame, and at the distal end of the frame the filter material is secured to the tube 50 adjacent to the coupling 76 by a coupling 84. Thus the filter material forms a cone when the filter 40 is expanded, and the open proximal end of the cone is positively closed when the proximal end row of cells of the central section 44 collapse against the tube 50.

As shown in FIG. 3, when the filter 40 moves along the guidewire 12 through the delivery tube 34, the mesh filter material 82 is enclosed within the frame 42 which protects the filter material. Also, when an expanded filter is contracted and drawn back into the delivery tube, the frame engages the delivery tube and precludes the filter from catching or snagging on the delivery tube.

FIGS. 4 and 5 disclose a positioning and recovery system 84 for the filter 40. This system includes an elongate, flexible, tubular member 86 having a docking end 88 for receiving the coupling 74 of the filter 40. The docking end is provided with a plurality of longitudinally extending lumens 90, two of which are shown in FIGS. 4 and 5, and an outwardly inclined hook 92 of flexible material, such as stainless steel, is mounted in each lumen to extend outwardly from the docking end of the tubular member 86.

When the filter 40 is collapsed within the delivery tube 34 as shown in FIG. 3, the tubular member 86 with the hooks 92 engaged with the cells 68 extends over the guidewire 12 to move the filter through the delivery tube. When the filter is ejected from the delivery tube and the hooks 92 extend outwardly from the end of the delivery tube, the hooks spring open as illustrated in FIG. 4 releasing the filter. If desirable, the filter can be moved further from the delivery tube by the engagement between the filter and the stepped docking end of the tubular member 86 before the delivery tube and the docking and positioning system are withdrawn.

To recover the filter, the tubular member 86 with the hooks 92 compressed as shown in FIG. 5 is passed through the delivery tube and outwardly therefrom until the hooks spring open and are positioned over the cells 68 as shown in FIG. 4. Now the delivery tube is moved over the hooks to compress and engage the hooks with the cells 68 as shown in FIG. 5, and once the hooks are engaged, the filter can be drawn back into the delivery tube by the tubular member 86.

I claim:

1. A free standing filter adapted to freely slide along an elongate guidewire not secured to said filter into a blood vessel and to expand radially into contact with the blood vessel wall and subsequent to expansion to permit free movement of said guidewire relative to said free standing filter without resulting in movement of said filter comprising:

a filter body having a first end and a second end spaced from said first end with a longitudinal axis extending between said first and second ends, said filter body including an elongate guidewire receiving member extending between the first and second ends of said filter body, said elongate guidewire receiving member defining a channel having two opposed open ends, said channel being sized to receive and permit passage of an elongate guidewire unsecured to said filter body through said elongate guidewire receiving member and outwardly beyond the two open ends thereof and to permit free relative movement between said filter body and said guidewire along the longitudinal axis of said filter body, an expandable and contractible frame connected to and surrounding said elongate guidewire receiving member, said frame being adapted to move between a first contracted position adjacent to said elongate guidewire receiving member and a second expanded position spaced radially from said elongate guidewire receiving member, and a porous embolic capturing unit connected to said frame, said frame being positioned externally of said porous embolic capturing unit, said porous embolic capturing unit in the second position of said frame being formed to define an enclosed chamber with a single open end spaced from a chamber closed end, said elongate guidewire receiving member extending through said chamber, the porous embolic capturing unit being connected to said guidewire receiving member at the chamber closed end and to said frame at said chamber single open end, said frame including an elongate central frame section surrounding and extending substantially parallel to said elongate guidewire receiving member, said elongate central frame section being positioned adjacent to said elongate guidewire receiving member in the first, contracted position of said frame and expanding into contact with said vessel wall in the second expanded position of said frame, a first end section extending between said elongate central frame section and said guidewire receiving member, said first end section being secured to said elongate guidewire receiving member and a second end section extending between said elongate central frame section and said elongate guidewire receiving member, said second end section being connected to said elongate guidewire receiving member for sliding movement relative thereto.

2. The free standing filter of claim 1 wherein said porous embolic capturing unit is connected to said elongate central frame section with said chamber single open end positioned adjacent to said first end section, said central frame section operating to close the open end of the enclosed chamber of said porous embolic capturing unit in the first contracted position of said frame and to open the open end of said enclosed chamber in the second expanded position of said frame, the porous embolic capturing unit extending into said second end section to a connection at the closed end thereof with said elongate guidewire receiving member.

3. The free standing filter of claim 2 wherein said porous embolic capturing unit is formed of expandable material which can be expanded from an unexpanded to an expanded configuration of said porous embolic capturing unit, said porous embolic capturing unit in the unexpanded configuration thereof being formed to engage and conform to an outer configuration of said elongate guidewire receiving member.

4. The free standing filter of claim 3 wherein said central frame section operates to expand said porous embolic capturing unit to the expanded configuration thereof in the second expanded position of said frame, said porous embolic capturing unit operating to bias said central frame section toward said elongate guidewire receiving member in the second expanded position of said frame.

5. The free standing filter of claim 4 wherein the open ended channel in said elongate guidewire receiving member is sized to receive guidewires having a plurality of sizes to permit a first guidewire having a first size to be used to introduce said filter into said blood vessel and to permit the withdrawal and replacement of said first guidewire with a second guidewire of a second size different from said first size after said frame is expanded.

6. The free standing filter of claim 5 wherein said open ended channel in said elongate guidewire receiving member is sized to receive guidewires sized within a range of from 0.014 inch diameter to 0.035 inch diameter.

7. The free standing filter of claim 5 wherein said frame is formed of thermal shape memory material.

8. A free standing filter adapted to freely slide along an elongate guidewire not secured to said filter into a blood vessel and to expand radially into contact with the blood vessel wall and subsequent to expansion to permit free movement of said guidewire relative to said free standing filter without resulting in movement of said filter comprising:

a filter body having a first end and a second end spaced from said first end with a longitudinal axis extending between said first and second ends, said filter body including an elongate guidewire receiving member extending between the first and second ends of said filter body, said elongate guidewire receiving member defining a channel having two opposed open ends, said channel being sized to receive and permit passage of an elongate guidewire unsecured to said filter body through said elongate guidewire receiving member and outwardly beyond the two open ends thereof and to permit free relative movement between said filter body and said guidewire along the longitudinal axis of said filter body, an expandable and contractible frame connected to and surrounding said elongate guidewire receiving member, said frame being adapted to move between a first contracted position adjacent to said elongate guidewire receiving member and a second expanded position spaced radially from said elongate guidewire receiving member, and a porous embolic capturing unit which is a flexible mesh unit connected to said frame, said elongate guidewire receiving member extending through said porous embolic capturing unit which in the second expanded position of said frame forms a substantially cylindrical open end section which opens toward the first end of said filter body and a flexible conical section extending from said cylindrical open end section and having a closed end connected to said elongate guidewire receiving member adjacent to the second end of said filter body, the flexible mesh unit being connected to said frame at the cylindrical open end section thereof, said frame being formed by a stent which is substantially cylindrical in the second expanded position of said frame, said stent being positioned in the cylindrical open end section of said flexible mesh unit, said flexible conical section of said flexible mesh unit extending outwardly from said stent, the closed end of said flexible conical section being connected to said elongate guidewire receiving member for sliding movement along said elongate guidewire receiving member.

9. The free standing filter of claim 8 wherein said stent is positioned externally of said flexible mesh unit and is connected to said elongate guidewire receiving member by a plurality of spaced, elongate connectors extending from said stent to a connection with said elongate guidewire receiving member adjacent to the first end of said filter body.

10. The free standing filter of claim 9 wherein said stent is formed of thermal shape memory material.

11. A free standing filter adapted to freely slide along an elongate guidewire not secured to said filter into a blood vessel and to expand radially into contact with the blood vessel wall and subsequent to expansion to permit free movement of said guidewire relative to said free standing filter without resulting in movement of said filter comprising:

a filter body having a first end and a second end spaced from said first end with a longitudinal axis extending between said first and second ends, said filter body including an elongate guidewire receiving member extending between the first and second ends of said filter body, said elongate guidewire receiving member defining a channel having two opposed open ends, said channel being sized to receive and permit passage of an elongate guidewire unsecured to said filter body through said elongate guidewire receiving member and outwardly beyond the two open ends thereof and to permit free relative movement between said filter body and said guidewire along the longitudinal axis of said filter body, an expandable and contractible frame connected to and surrounding said elongate guidewire receiving member, said frame being adapted to move between a first contracted position adjacent to said elongate guidewire receiving member and a second expanded position spaced radially from said elongate guidewire receiving member, and a porous embolic capturing unit which is a flexible mesh unit connected to said frame, said elongate guidewire receiving member extending through said porous embolic capturing unit which in the second expanded position of said frame forms a substantially cylindrical open end section which opens toward the first end of said filter body and a flexible conical section extending from said cylindrical open end section and having a closed end connected to said elongate guidewire receiving member adjacent to the second end of said filter body, the flexible mesh unit being connected to said frame at the cylindrical open end section thereof, said frame in the second expanded position includes a substantially cylindrical center section, a first substantially conical end section extending outward from said center section which is connected to said elongate guidewire receiving member adjacent to the first end of said filter body and a second substantially conical end section extending outwardly from said center section which is connected to said elongate guidewire receiving member adjacent to the second end of said filter body.

12. The free standing filter of claim 11 wherein said frame is positioned externally of said flexible mesh unit.

13. The free standing filter of claim 12 wherein said second substantially conical end section of said frame is connected to said elongate guidewire receiving member for sliding movement along said elongate guidewire receiving member.

14. The free standing filter of claim 13 wherein said frame is formed of thermal shape memory material.

15. The free standing filter of claim 14 wherein said flexible mesh unit is elastic and formed to engage and conform to an outer configuration of said elongate guidewire receiving member in the first contracted position of said frame and to elastically expand and bias said frame toward said first position when said frame moves to the second expanded position.

\* \* \* \* \*